(12) United States Patent
Sechrist et al.

(10) Patent No.: US 7,271,303 B1
(45) Date of Patent: Sep. 18, 2007

(54) MULTI-ZONE PROCESS FOR THE PRODUCTION OF DIESEL AND AROMATIC COMPOUNDS

(75) Inventors: Paul A. Sechrist, South Barrington, IL (US); Stanley J. Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 539 days.

(21) Appl. No.: 10/946,928

(22) Filed: Sep. 22, 2004

(51) Int. Cl.
 *C07C 4/02* (2006.01)
 *C07C 6/00* (2006.01)
 *C10G 47/00* (2006.01)

(52) U.S. Cl. .................. 585/319; 585/475; 208/108

(58) Field of Classification Search ................ 585/319, 585/475; 208/108, 134
See application file for complete search history.

(56) References Cited

U.S. PATENT DOCUMENTS

| | | | |
|---|---|---|---|
| 2,620,314 A | 12/1952 | Hoekstra | 252/448 |
| 2,892,858 A | 6/1959 | Ziegler | 260/448 |
| 3,130,006 A | 4/1964 | Rabo et al. | 23/110 |
| 3,702,886 A | 11/1972 | Argauer et al. | 423/328 |
| 3,709,979 A | 1/1973 | Chu | 423/328 |
| 3,832,449 A | 8/1974 | Rosinski et al. | 423/328 |
| 3,849,340 A | 11/1974 | Pollitzer | 252/455 Z |
| 3,852,190 A | 12/1974 | Buss et al. | 208/138 |
| RE28,341 E | 2/1975 | Wadlinger et al. | 208/120 |
| 4,012,313 A | 3/1977 | Buss et al. | 208/139 |
| 4,053,388 A | 10/1977 | Bailey | 208/89 |
| 4,076,842 A | 2/1978 | Plank et al. | 423/328 |
| 4,127,471 A | 11/1978 | Suggitt et al. | 208/60 |
| 4,159,282 A | 6/1979 | Olson et al. | 585/481 |
| 4,163,018 A | 7/1979 | Tada et al. | 260/429.9 |
| 4,241,036 A | 12/1980 | Flanigen et al. | 423/328 |
| 4,276,437 A | 6/1981 | Chu | 585/467 |
| 4,278,565 A | 7/1981 | Chen et al. | 252/455 Z |
| 4,341,914 A | 7/1982 | Berger | 585/474 |
| 4,363,718 A | 12/1982 | Klotz | 208/110 |
| 4,440,871 A | 4/1984 | Lok et al. | 502/214 |
| 4,537,754 A | 8/1985 | Casci et al. | 423/277 |
| 4,556,477 A | 12/1985 | Dwyer | 208/111 |
| 4,567,029 A | 1/1986 | Wilson et al. | 423/306 |
| 4,923,595 A | 5/1990 | Moser et al. | 208/139 |
| 5,296,208 A | 3/1994 | Lesch | 423/700 |
| 5,723,710 A | 3/1998 | Gajda et al. | 585/467 |
| 5,763,720 A | 6/1998 | Buchanan et al. | 585/475 |
| 5,847,256 A | 12/1998 | Ichioka et al. | 585/470 |

FOREIGN PATENT DOCUMENTS

EP 0 378 916 B1 11/1992

*Primary Examiner*—Thuan Dinh Dang
(74) *Attorney, Agent, or Firm*—David J. Piasecki (57) ABSTRACT

A multi-zone process for the production of low sulfur diesel and aromatic compounds wherein $C_9^+$ hydrocarbons are hydrocracked to produce low sulfur diesel and a naphtha boiling range stream which is reformed and transalkylated within reforming and transalkylation zones to produce an aromatics-rich high-octane stream containing xylene and to balance hydrogen needs.

25 Claims, 1 Drawing Sheet

MULTI-ZONE PROCESS FOR THE PRODUCTION OF DIESEL AND AROMATIC COMPOUNDS

BACKGROUND OF THE INVENTION

This invention relates to a process for the conversion of a hydrocarbon feedstock to produce low sulfur diesel and aromatic compounds including xylenes. More specifically, the invention concerns the selective hydrocracking of multi-ring aromatic compounds contained in the hydrocarbon feedstock to produce low sulfur diesel and naphtha-range aromatic compounds via integrated reforming and transalkylation zones that produce the most desirable xylene isomers and balance hydrogen demand.

It has been recognized that due to environmental concerns and newly enacted rules and regulations, saleable products must meet lower and lower limits on contaminants such as sulfur and nitrogen. Recently new regulations require the essentially complete removal of sulfur from liquid hydrocarbons which are used in transportation fuels, such as gasoline and diesel.

The xylene isomers are produced in large volumes from petroleum as feedstocks for a variety of important industrial chemicals. The most important of the xylene isomers is paraxylene, the principal feedstock for polyester which continues to enjoy a high growth rate from a large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less desirable component of $C_8$ aromatics.

Among the aromatic hydrocarbons, the overall importance of the xylenes rivals that of benzene as a feedstock for industrial chemicals. Neither the xylenes nor benzene are directly produced from petroleum by the reforming of naphtha in sufficient volume to meet demand; thus conversion of other hydrocarbons is necessary to increase the yield of xylenes and benzene.

INFORMATION DISCLOSURE

U.S. Pat. No. 5,847,256 to Ichioka et al. discloses a process for producing xylene from a feedstock containing $C_9$ alkylaromatics with the aid of a catalyst with a zeolite that is preferably mordenite and with a metal that is preferably rhenium.

U.S. Pat. No. 5,763,720 to Buchanan et al. discloses a transalkylation process for producing benzene and xylenes by contacting a $C_9^+$ alkylaromatics with benzene and/or toluene over a catalyst comprising a zeolite such as ZSM-12 and a hydrogenation noble metal such as platinum.

U.S. Pat. No. 4,923,595 to Moser et al. discloses a multi-zone naphtha reforming process based on a combination of catalysts that variously use platinum with germanium, rhenium, tin, and other metal modifiers.

U.S. Pat. No. 4,341,914 to Berger discloses a transalkylation process with recycle of $C_{10}$ alkylaromatics in order to increase yield of xylenes from the process.

U.S. Pat. No. 4,276,437 to Chu discloses transalkylation and disproportionation of alkylaromatics to yield predominantly the 1,4-alkylaromatic isomer using a zeolite which has been modified by treatment with a compound of a Group IIIB element and may contain phosphorus.

U.S. Pat. No. 4,127,471 to Suggitt et al. discloses a process for hydrocracking a charge stock at mild hydrocracking conditions followed by alkyl transfer.

U.S. Pat. No. 4,053,388 to Bailey discloses a process for preparing aromatics from naphtha that achieves an increased yield by integrating a catalytic reforming unit with a thermal hydrocracking unit.

SUMMARY OF THE INVENTION

The present invention is a process for the production of low sulfur diesel and aromatic compounds wherein a hydrocarbonaceous feedstock containing multi-ring aromatic compounds is hydrocracked in a hydrocracking zone and partially converted to preferably produce diesel and xylenes. The effluent from the hydrocracking zone is separated to produce a stream comprising hydrocarbons boiling in the naphtha range and a hydrocarbon stream boiling in the range above naphtha which contains low sulfur diesel and which may be further hydrotreated to saturate aromatic compounds thereby improving the cetane rating. At least a portion of the hydrocarbons boiling in the naphtha range is introduced into a reforming zone and optionally into a transalkylation zone. Hydrogen produced in the reforming zone is introduced into the transalkylation zone and is also introduced into the hydrocracking zone.

DETAILED DESCRIPTION OF THE INVENTION

The process of the present invention is particularly useful for the production of xylene and diesel from a hydrocarbon feedstock. Suitable hydrocarbon feedstocks boil in the range from about 149° C. (300° F.) to about 399° C. (750° F.) and preferably contain at least about 50 vol-% aromatic compounds. Particularly preferred feedstocks contain at least a portion of light cycle oil (LCO) which is a by-product of the fluid catalytic cracking (FCC) process. LCO is an economical and advantageous feedstock since it is undesirable as a finished product and contains significant quantities of sulfur, nitrogen and polynuclear aromatic compounds. Therefore, the present invention is able to convert a low-value LCO stream into valuable xylene hydrocarbon compounds and diesel.

In one preferred embodiment of the present invention, the selected feedstock is first introduced into a denitrification and desulfurization reaction zone together with a liquid recycle stream and hydrogen at hydrotreating reaction conditions. Preferred denitrification and desulfurization reaction conditions or hydrotreating reaction conditions include a temperature from about 204° C. (400° F.) to about 482° C. (900° F.), a pressure from about 3.5 MPa (500 psig) to about 17.3 MPa (2500 psig), a liquid hourly space velocity of the fresh hydrocarbonaceous feedstock from about 0.1 to about 10 $hr^{-1}$ with a hydrotreating catalyst or a combination of hydrotreating catalysts.

The term "hydrotreating" as used herein refers to processes wherein a hydrogen-containing treat gas is used in the presence of suitable catalysts which are primarily active for the removal of heteroatoms, such as sulfur and nitrogen. Suitable hydrotreating catalysts for use in the present invention are any known conventional hydrotreating catalyst and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present invention that more than one type of hydrotreating catalyst be used in the same reaction vessel. The Group VIII metal is typically present in an amount ranging from about 2 to about 20 wt-%, preferably from about 4 to about 12 wt-%. The Group VI metal will typically be present in an amount ranging from about 1 to about 25 wt-%, preferably from about 2 to about 25 wt-%. Typical hydrotreating temperatures range from about 204° C. (400° F.) to about 482° C. (900° F.) with pressures from about 3.5 MPa (500 psig) to about 17.3 MPa (2500 psig), preferably from about 3.5 MPa (500 psig) to about 13.9 MPa (2000 psig).

In accordance with a preferred embodiment of the present invention, the resulting effluent from the denitrification and desulfurization zone is introduced into a hydrocracking zone. The hydrocracking zone may contain one or more beds of the same or different catalyst. In one embodiment the preferred hydrocracking catalysts utilize amorphous bases or low-level zeolite bases combined with one or more Group VIII or Group VIB metal hydrogenation components. In another embodiment, the hydrocracking zone contains a catalyst which comprises, in general, any crystalline zeolite cracking base upon which is deposited a minor proportion of a Group VIII metal hydrogenating component. Additional hydrogenation components may be selected from Group VIB for incorporation with the zeolite base. The zeolite cracking bases are sometimes referred to in the art as molecular sieves and are usually composed of silica, alumina and one or more exchangeable cations such as sodium, magnesium, calcium, rare earth metals, etc. They are further characterized by crystal pores of relatively uniform diameter between about 4 and 14 angstroms. It is preferred to employ zeolites having a silica/alumina mole ratio between about 3 and 12. Suitable zeolites found in nature include, for example, mordenite, stillbite, heulandite, ferrierite, dachiardite, chabazite, erionite and faujasite. Suitable synthetic zeolites include, for example, the B, X, Y and L crystal types, e.g., synthetic faujasite and mordenite. The preferred zeolites are those having crystal pore diameters between about 8 and 12 angstroms, wherein the silica/alumina mole ratio is about 4 to 6. A prime example of a zeolite falling in the preferred group is synthetic Y molecular sieve.

The natural occurring zeolites are normally found in a sodium form, an alkaline earth metal form, or mixed forms. The synthetic zeolites are nearly always prepared first in the sodium form. In any case, for use as a cracking base it is preferred that most or all of the original zeolitic monovalent metals be ion-exchanged with a polyvalent metal and/or with an ammonium salt followed by heating to decompose the ammonium ions associated with the zeolite, leaving in their place hydrogen ions and/or exchange sites which have actually been decationized by further removal of water. Hydrogen or "decationized" Y zeolites of this nature are more particularly described in U.S. Pat. No. 3,130,006.

Mixed polyvalent metal-hydrogen zeolites may be prepared by ion-exchanging first with an ammonium salt, then partially back exchanging with a polyvalent metal salt and then calcining. In some cases, as in the case of synthetic mordenite, the hydrogen forms can be prepared by direct acid treatment of the alkali metal zeolites. The preferred cracking bases are those which are at least about 10 percent, and preferably at least 20 percent, metal-cation-deficient, based on the initial ion-exchange capacity. A specifically desirable and stable class of zeolites are those wherein at least about 20 percent of the ion exchange capacity is satisfied by hydrogen ions.

The active metals employed in the preferred hydrocracking catalysts of the present invention as hydrogenation components are those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten. The amount of hydrogenating metal in the catalyst can vary within wide ranges. Broadly speaking, any amount between about 0.05 percent and 30 percent by weight may be used. In the case of the noble metals, it is normally preferred to use about 0.05 to about 2 wt-%. The preferred method for incorporating the hydrogenating metal is to contact the zeolite base material with an aqueous solution of a suitable compound of the desired metal wherein the metal is present in a cationic form. Following addition of the selected hydrogenation metal or metals, the resulting catalyst powder is then filtered, dried, pelleted with added lubricants, binders or the like, if desired, and calcined in air at temperatures of e.g., 371° to 648° C. (700° to 1200° F.) in order to activate the catalyst and decompose ammonium ions. Alternatively, the zeolite component may first be pelleted, followed by the addition of the hydrogenating component and activation by calcining. The foregoing catalysts may be employed in undiluted form, or the powdered zeolite catalyst may be mixed and copelleted with other relatively less active catalysts, diluents or binders such as alumina, silica gel, silica-alumina cogels, activated clays and the like in proportions ranging between 5 and 90 wt-%. These diluents may be employed as such or they may contain a minor proportion of an added hydrogenating metal such as a Group VIB and/or Group VIII metal.

Additional metal promoted hydrocracking catalysts may also be utilized in the process of the present invention which comprises, for example, aluminophosphate molecular sieves, crystalline chromosilicates and other crystalline silicates. Crystalline chromosilicates are more fully described in U.S. Pat. No. 4,363,718.

The hydrocracking of the hydrocarbonaceous feedstock in contact with a hydrocracking catalyst is conducted in the presence of hydrogen and preferably at hydrocracking reactor conditions which include a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 $hr^{-1}$, and a hydrogen circulation rate from about 84 normal $m^3/m^3$ (500 standard cubic feet per barrel) to about 4200 $m^3/m^3$ (25,000 standard cubic feet per barrel). In accordance with the present invention, the hydrocracking conditions are selected on the basis of the feedstock with the objective of the production of xylene compounds and low sulfur diesel.

A hydrotreating/hydrocracking zone may contain one or more vessels or beds each containing one or more types of hydrotreating catalyst or hydrocracking catalyst. When a liquid hydrocarbon stream is recycled to the hydrotreating/hydrocracking zone, the recycle stream may be introduced directly into a hydrocracking catalyst, or may be passed through a bed of hydrotreating catalyst and then contacted with the hydrocracking catalyst.

The resulting effluent from the hydrocracking zone is introduced into a main fractionator. In one embodiment, the main fractionator is a hot, high pressure stripper to produce a first vaporous stream comprising hydrogen, hydrogen sulfide, ammonia and naphtha boiling range hydrocarbons including $C_{10}^-$ aromatic hydrocarbons, and a second liquid hydrocarbonaceous stream comprising diesel boiling range hydrocarbons. The hot, high pressure stripper is preferably operated at a temperature from about 149° C. (300° F.) to about 288° C. (550° F.) and a pressure from about 3.5 MPa (500 psig) to about 17.3 MPa (2500 psig). In another embodiment, the main fractionator is a column operating at a lower pressure, such as atmospheric pressure, and operating without specific hydrogen stripping. The main fractionator column also produces a first stream comprising hydrogen, hydrogen sulfide, ammonia and naphtha boiling range hydrocarbons including $C_{10}^-$ aromatic hydrocarbons, and a second stream comprising diesel boiling range hydrocarbons The first stream is at least partially condensed as needed to produce a liquid hydrocarbon stream comprising hydrocarbons boiling in the range from about 38° C. (100° F.) to about 220° C. (428° F.) including $C_{10}^-$ aromatic hydrocarbons. And such condensation as needed also produces a vapor stream comprising hydrogen, hydrogen sulfide and ammonia, which vapor stream, is treated to remove hydrogen sulfide and ammonia to provide a hydrogen-rich recycle gas. At least a portion of the condensed liquid hydrocarbon stream is secondarily fractionated with optional stripping to remove normally gaseous hydrocarbon compounds and any dissolved hydrogen sulfide and ammonia.

The resulting secondarily fractionated naphtha boiling range hydrocarbon stream is then further fractionated to separate benzene, toluene, xylenes and higher boiling aromatic compounds. In a preferred embodiment, at least a portion of the benzene and toluene, and the 9 and 10 carbon number aromatic compounds are introduced as a naphtha feedstock into a reforming zone and then into transalkylation zone to enhance the production of xylene compounds. The reforming zone and transalkylation zone may contain one or more beds of the same or different catalyst, and such beds may be disposed in one or more vessels. The zones may be integrated together in connected serial processes using multiple vessels or directly coupled together. An integrated reforming-transalkylation zone may contain one or more vessels or beds each containing one or more types of reforming catalyst and/or transalkylation catalyst. Such types of catalyst are optionally segregated or are mixed together either in a bulk physical mixture or in a micro particulate mixture with dual catalytic functions composited on the same particles. In another embodiment, the above described resulting secondarily fractionated naphtha boiling range hydrocarbon stream is not further fractionated and is instead passed directly to a reforming zone.

In the reforming zone, naphtha hydrocarbon feedstock and a hydrogen-rich gas are preheated and charged to a reaction zone containing typically one to five reactors in series. Suitable heating means are provided between reactors to compensate for the net endothermic heat of reaction in each of the reactors. Reactants may contact the catalyst in individual reactors in upflow, downflow, or radial flow fashion. The catalyst is contained in a fixed-bed system or in a moving-bed system with associated continuous catalyst regeneration. Alternative approaches to reactivation of deactivated catalyst are well known to those skilled in the art, and include semi-regenerative operation in which the entire unit is shut down for catalyst regeneration and reactivation or swing-reactor operation in which an individual reactor is isolated from the system, regenerated and reactivated while the other reactors remain on-stream.

Effluent from the reforming zone is passed through a cooling means to an optional separation zone, typically maintained at about 0° to 65° C., wherein a hydrogen-rich gas is separated from a liquid stream commonly called "unstabilized reformate". The resultant hydrogen stream can then be recycled through suitable compressing means back to the reforming zone. The liquid phase from the separation zone is typically withdrawn and processed in a fractionating system in order to adjust the butane concentration, thereby controlling front-end volatility of the resulting reformate. Alternatively, the fractionating system for the liquid phase may be omitted, and reformate may be passed directly to the subsequent transalkylation zone. Such reformate regardless of fractionation may also be recovered as a gasoline product with high octane value.

Reforming conditions applied in the reforming zone of the present invention include a pressure selected within the range of about 100 kPa (14.7 psig) to 7 MPa (1000 psig). Particularly good results are obtained at low pressure, namely a pressure of about 350 (50 psig) to 2750 kPa (400 psig). Reforming temperature is in the range from about 177° C. (350° F.) to about 565° C. (1049° F.). As is well known to those skilled in the reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant octane product. Sufficient hydrogen is supplied by recirculation from the reforming effluent or from other hydrogen sources to thereby provide an amount of about 1 to about 20 moles of hydrogen per mole of hydrocarbon feed entering the reforming zone, with excellent results being obtained when about 2 to about 10 moles of hydrogen are used per mole of hydrocarbon feed. Likewise, the liquid hourly space velocity used in reforming is selected from the range of about 0.2 to about 20 $hr^{-1}$.

The hydrogen-rich gaseous stream from the reforming zone is introduced into the transalkylation zone and is also introduced into the hydrocracking zone as make-up hydrogen. This gaseous stream is the primary make-up hydrogen to the integrated process and preferably contains at least 80 mol-% hydrogen with essentially no hydrogen sulfide or ammonia. Operating conditions preferably employed in the integrated reforming-transalkylation zone normally include a temperature from about 177° C. (350° F.) to about 550° C. (1022° F.) and a liquid hourly space velocity in the range from about 0.2 to about 10 $hr^{-1}$.

In the optional transalkylation zone, the reformate feedstock is preferably transalkylated in the vapor phase and in the presence of hydrogen. Aromatic hydrocarbons of carbon number nine and above may also be fed directly to the transalkylation zone part and thus bypass the reforming zone part. This heavy aromatic stream bypass can also be used as a heat sink to control any temperature differential needed between the reforming zone outlet and transalkylation zone inlet. If feedstock is transalkylated in the liquid phase, then the presence of hydrogen is optional. If present, free hydrogen is associated with the feedstock and recycled hydrocarbons in an amount of from about 0.1 moles per mole of alkylaromatics up to 10 moles per mole of alkylaromatic.

This ratio of hydrogen to alkylaromatic is also referred to as hydrogen to hydrocarbon ratio. The transalkylation reaction preferably yields a product having an increased xylene content and also comprises toluene.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. The use of a single reaction vessel having a fixed cylindrical bed of transalkylation catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a fractionation column in which substantially all $C_5$ and lighter hydrocarbons present in the effluent are concentrated into an overhead stream and removed from the process. An aromatics-rich stream is recovered as net column bottoms.

To effect a transalkylation reaction, the present invention incorporates a transalkylation catalyst in at least one zone, but no limitation is intended in regard to a specific catalyst. Conditions employed in the transalkylation zone normally include a temperature of from about 200° C. (392° F.) to about 540° C. (1004° F.). The transalkylation zone is operated at moderately elevated pressures broadly ranging from about 100 kPa (14.7 psig) to about 6 MPa (870 psig). The transalkylation reaction can be effected over a wide range of space velocities. Liquid hourly space velocity generally ranges from about 0.1 to about 20 $hr^{-1}$.

It is a preferred practice to operate the reforming zone of the present invention in a substantially sulfur-free environment. Any guard bed control means known in the art may be used to treat the naphtha feedstock which is to be charged to the reforming reaction zone. For example, the feedstock may be subjected to guard bed adsorption processes, guard bed catalytic processes, or combinations thereof. Preferred guard bed adsorption processes may employ adsorbents such as molecular sieves, high surface area aluminas, high surface area silica-aluminas, carbon molecular sieves, crystalline aluminosilicates, activated carbons, and high surface area metallic containing compositions, such as nickel or copper and the like. Guard beds may be loaded in separate vessels in the reforming zone or the hydrocracking zone, or guard beds may be loaded inside the catalyst vessel or vessels themselves. Guard beds may also be loaded in conjunction with the transalkylation zone as needed to deal with any contaminants such as sulfur or chloride that may arise from specific streams passing over the transalkylation catalyst.

Any suitable reforming catalyst may be utilized in the reforming zone. Preferred reforming catalysts contain a solid refractory oxide support having dispersed thereon at least one platinum group metal component and optionally a modifier metal component such as tin or rhenium. The support can be any of a number of well-known supports in the art including aluminas, silica/alumina, silica, titania, zirconia, and zeolites. The aluminas which can be used as support include gamma alumina, theta alumina, delta alumina, and alpha alumina with gamma and theta alumina being preferred. Included among the aluminas are aluminas which contain modifiers such as tin, zirconium, titanium and phosphate. The zeolites which can be used include: faujasites, zeolite beta, L zeolite, ZSM 5, ZSM 8, ZSM 11, ZSM 12 and ZSM 35. The supports can be formed in any desired shape such as spheres, pills, cakes, extrudates, powders, granules, etc. and they may be utilized in any particular size.

One way of preparing a spherical alumina support is by the well known oil drop method which is described in U.S. Pat. No. 2,620,314. The oil drop method comprises forming an aluminum hydrosol by any of the techniques taught in the art and preferably by reacting aluminum metal with hydrochloric acid; combining the hydrosol with a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged and gelled spheres are then washed and dried at a relatively low temperature of about 80° to 260° C. and then calcined at a temperature of about 455° to 705° C. for a period of about 1 to about 20 hours. This treatment effects conversion of the hydrogel to the corresponding crystalline gamma alumina. If theta alumina is desired then the hydrogel spheres are calcined at a temperature of about 950° to about 1100° C.

An alternative form of carrier material is a cylindrical extrudate, preferably prepared by mixing the alumina powder with water and suitable peptizing agents such as HCl until an extrudable dough is formed. The resulting dough is extruded through a suitably sized die to form extrudate particles. These particles are then dried at a temperature of about 260° to about 427° C. for a period of about 0.1 to 5 hours to form the extrudate particles. It is preferred that the refractory inorganic oxide comprises substantially pure alumina. A typical substantially pure alumina has been characterized in U.S. Pat. No. 3,852,190 and U.S. Pat. No. 4,012,313 as a by-product from a Ziegler higher alcohol synthesis reaction as described in Ziegler's U.S. Pat. No. 2,892,858.

An essential ingredient of the reforming catalyst is a dispersed platinum-group component. This platinum-group component may exist within the final catalytic composite as a compound such as an oxide, sulfide, halide, oxyhalide, etc., in chemical combination with one or more of the other ingredients of the composite or as an elemental metal. It is preferred that substantially all of this component is present in the elemental state and is uniformly dispersed within the support material. This component may be present in the final catalyst composite in any amount which is catalytically effective, but relatively small amounts are preferred. Of the platinum-group metals which can be dispersed on the desired support, preferred metals are rhodium, palladium, platinum, and platinum being most preferred.

A Group IVA (IUPAC 14) metal component is an optional ingredient of the reforming catalyst. Of the Group IVA (IUPAC 14) metals, germanium and tin are preferred and tin is especially preferred. This component may be present as an elemental metal, as a chemical compound such as the oxide, sulfide, halide, oxychloride, etc., or as a physical or chemical combination with the porous carrier material and/or other components of the catalytic composite. Preferably, a substantial portion of the Group IVA (IUPAC 14) metal exists in the finished catalyst in an oxidation state above that of the elemental metal.

Rhenium is also an optional metal promoter of the reforming catalyst. In addition to the catalytic components described above, other components may be added to the catalyst. For example, a modifier metal selected from the non-exclusive list of lead, indium, gallium, iridium, lanthanum, cerium, phosphorous, cobalt, nickel, iron and mixtures thereof may be added to the reforming catalyst.

Another optional component of the reforming catalyst, particularly useful in embodiments of the present invention comprising dehydrogenation, dehydrocyclization, or hydrogenation reactions, is an alkali or alkaline-earth metal component. More precisely, this optional ingredient is selected from the group consisting of the compounds of the alkali metals—cesium, rubidium, potassium, sodium, and lithium—and the compounds of the alkaline earth metals—calcium, strontium, barium, and magnesium.

Any suitable transalkylation catalyst may be utilized in the transalkylation zone. Preferred transalkylation catalysts contain a solid-acid material combined with an optional metal component. Suitable solid-acid materials include all forms and types of mordenite, mazzite (omega zeolite), beta zeolite, ZSM-11, ZSM-12, ZSM-22, ZSM-23, MFI type zeolite, NES type zeolite, EU-1, MAPO-36, MAPSO-31, SAPO-5, SAPO-11, SAPO-41, and silica-alumina or ion exchanged versions of such solid-acids. For example, in U.S. Pat. No. 3,849,340 a catalytic composite is described comprising a mordenite component having an $SiO_2/Al_2O_3$ mole ratio of at least 40:1 prepared by acid extracting $Al_2O_3$ from mordenite prepared with an initial $SiO_2/Al_2O_3$ mole ratio of less than 30:1 and a metal component selected from copper, silver and zirconium. Refractory inorganic oxides, combined with the above-mentioned and other known catalytic materials, have been found useful in transalkylation operations. For instance, silica-alumina is described in U.S. Pat. No. 5,763,720. Crystalline aluminosilicates have also been employed in the art as transalkylation catalysts. ZSM-12 is more particularly described in U.S. Pat. No. 3,832,449. Zeolite beta is more particularly described in Re. 28,341 (of original U.S. Pat. No. 3,308,069). A favored form of zeolite beta is described in U.S. Pat. No. 5,723,710, which is incorporated herein by reference. The preparation of MFI topology zeolite is also well known in the art. In one method, the zeolite is prepared by crystallizing a mixture containing an alumina source, a silica source, an alkali metal source, water and an alkyl ammonium compound or its precursor. Further descriptions are in U.S. Pat. No. 4,159,282, U.S. Pat. No. 4,163,018, and U.S. Pat. No. 4,278,565. The synthesis of the Zeolite Omega is described in U.S. Pat. No. 4,241,036. ZSM intermediate pore size zeolites useful in this invention include ZSM-5 (U.S. Pat. No. 3,702,886); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842). European Patent EP 0378916 B1 describes NES type zeolite and a method for preparing NU-87. The EUO structural-type EU-1 zeolite is described in U.S. Pat. No. 4,537,754. MAPO-36 is described in U.S. Pat. No. 4,567,029. MAPSO-31 is described in U.S. Pat. No. 5,296,208 and typical SAPO compositions are described in U.S. Pat. No. 4,440,871 including SAPO-5, SAPO-11 and SAPO-41.

A refractory binder or matrix is optionally utilized to facilitate fabrication of the transalkylation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder.

The transalkylation catalyst also may contain an optional metal component. One preferred metal component is a Group VIII (IUPAC 8-10) metal that includes nickel, iron, cobalt, and platinum-group metal. Of the platinum group, i.e., platinum, palladium, rhodium, ruthenium, osmium and iridium, platinum is especially preferred. Another preferred metal component is rhenium and it will be used for the general description that follows. This metal component may exist within the final catalytic composite as a compound such as an oxide, sulfide, halide, or oxyhalide, in chemical combination with one or more of the other ingredients of the composite. The rhenium metal component may be incorporated in the catalyst in any suitable manner, such as coprecipitation, ion-exchange, co-mulling or impregnation. The preferred method of preparing the catalyst involves the utilization of a soluble, decomposable compound of rhenium metal to impregnate the carrier material in a relatively uniform manner. Typical rhenium compounds which may be employed include ammonium perrhenate, sodium perrhenate, potassium perrhenate, potassium rhenium oxychloride, potassium hexachlororhenate (IV), rhenium chloride, rhenium heptoxide, perrhenic acid, and the like compounds. Preferably, the compound is ammonium perrhenate or perrhenic acid because no extra steps may be needed to remove any co-contaminant species.

The transalkylation catalyst may optionally contain additional metal components along with those metal components discussed above or include additional metal components instead of those metal components in their entirety. Additional metal components of the catalyst include, for example, tin, germanium, lead, and indium and mixtures thereof. Catalytically effective amounts of such additional metal components may be incorporated into the catalyst by any means known in the art.

The resulting effluent from the reforming and optional transalkylation zones is introduced into a vapor-liquid separator to provide a hydrogen-rich gaseous stream which is compressed and used as make-up hydrogen for the hydrocracking zone. The naphtha boiling range liquid hydrocarbon from the vapor-liquid separator is fractionated to remove hydrocarbons boiling at a temperature lower than benzene and then sent to another fractionation section to separate benzene, toluene, xylenes and higher boiling aromatic compounds. In a preferred embodiment, the benzene and toluene would be recycled to the transalkylation zone to maximize the yield of the most valuable xylenes. In the event that more benzene and toluene is desired at the expense of xylene production, they may be directed to product tanks. For example, if the operator wishes to produce additional high octane gasoline, the benzene/toluene net product flow rate would be increased and the overall xylene production would thereby decrease. This readily available feature affords a very flexible way to produce different product slates.

In accordance with the present invention, the hydrogen make-up gas produced in the reforming zone may be compressed in a first stage compressor to a pressure suitable for introduction into the transalkylation zone. After optionally flowing through the transalkylation zone, the hydrogen-rich gas may be separated and sent to a second stage compressor whereinafter the hydrogen-rich gas is sent to four potential locations, namely, 1) stripping gas service for the hot high pressure stripper; 2) naphtha stripper, or secondary fractionation column; 3) make-up gas to an aromatic hydrogenation zones; and 4) make-up gas directly to the hydrocracking zone. The optional cascaded use of hydrogen make-up gas first through the transalkylation zone eliminates the need for a separate recycle gas compressor for the transalkylation zone or for the aromatic hydrogenation zone. The hydrogen-rich gas from the top of the naphtha stripper, or secondary fractionation column, is preferably amine treated to remove hydrogen sulfide and water washed to remove ammonia and sent to the hydrocracking zone recycle gas compressor which then sends the recycle hydrogen gas to two potential locations, namely, the aromatic hydrogenation zone and the hydrocracking zone.

The liquid hydrocarbon stream recovered from the bottom of the hot, high pressure stripper, or the second stream from the main fractionator column, (boiling generally above the boiling range of naphtha and in the boiling range of diesel) may have in one embodiment a portion recycled to the hydrocracking zone and in a second embodiment have at least a portion reacted in an aromatic hydrogenation zone. Any suitable hydrotreating catalyst may be utilized to hydrogenate the aromatic compounds in order to improve the cetane number. In another embodiment, the entire stream may be recovered as a low sulfur diesel product stream.

DETAILED DESCRIPTION OF THE DRAWING

Figure 1:
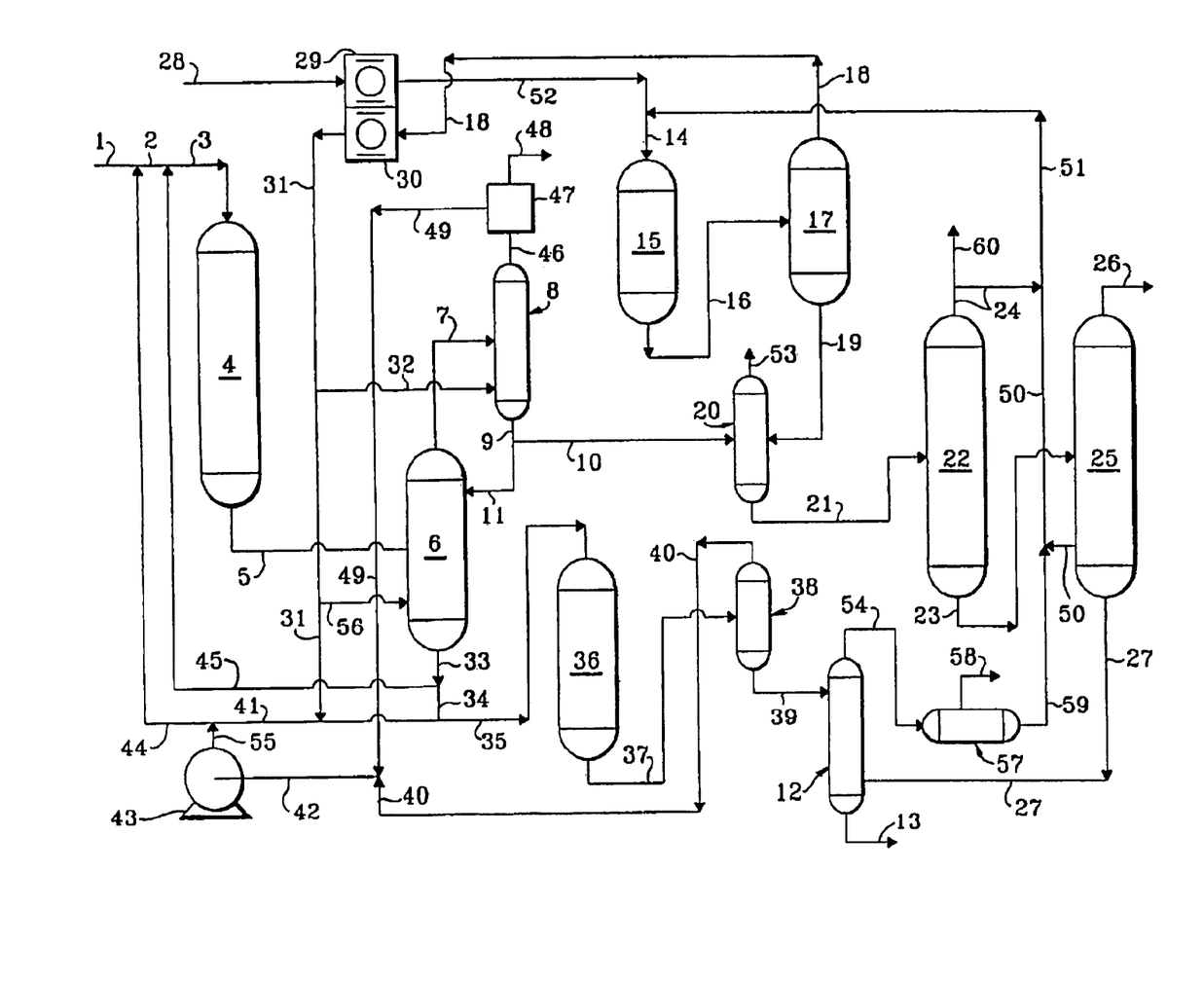
The drawing is a simplified process flow diagram of a preferred embodiment of the present invention. The above described drawing is intended to be schematically illustrative of the present invention and is not to be a limitation thereof.

The drawing is a simplified process flow diagram of a preferred embodiment of the present invention. The drawing is intended to be schematically illustrative of the present invention and not to be a limitation thereof.

A liquid hydrocarbonaceous feedstock containing light cycle oil is introduced into the process via line 1 and is admixed with a hereinafter described hydrogen-rich gaseous stream provided by line 44. The resulting admixture is transported via line 2 and is joined by a hereinafter described liquid hydrocarbonaceous recycle stream provided by line 45. This resulting admixture is transported via line 3 and introduced into hydrotreating/hydrocracking zone 4. The resulting effluent from hydrotreating/hydrocracking zone 4 is transported via line 5 and introduced into fractionation zone 6. A stream is removed from fractionation zone 6 via line 7, partially condensed as needed and introduced into fractionation zone 8. A hydrogen-rich gaseous stream is removed from fractionation zone 8 via line 46 and introduced into amine scrubber 47. Hydrogen sulfide and ammonia are removed from amine scrubber 47 via line 48 and recovered. A hydrogen-rich gaseous stream having a reduced concentration of hydrogen sulfide and ammonia is removed from amine scrubber 47 and is transported via line 49. A liquid hydrocarbonaceous stream containing naphtha is removed from fractionation zone 8 via line 9 and a portion is introduced into fractionation zone 6 via line 11 as reflux and another portion is transported via line 10 and introduced into fractionation zone 20. A hydrogen-rich gaseous stream containing essentially no hydrogen sulfide is introduced via line 28 into first stage makeup compressor 29 and the resulting compressed hydrogen-rich gas is transported via line 52 and introduced when needed via line 14 into reforming/transalkylation zone 15. A resulting effluent from transalkylation zone 15 is transported via line 16 and introduced into vapor liquid separator 17. A hydrogen-rich gaseous stream is removed from vapor liquid separator 17 via line 18 and introduced into second stage makeup compressor 30 to produce a compressed hydrogen-rich gaseous stream carried via line 31. A liquid hydrocarbonaceous stream containing transalkylated hydrocarbons is removed from vapor liquid separator 17 via line 19 and introduced into fractionation zone 20. A vaporous stream containing normally gaseous hydrocarbons is removed from fractionation zone 20 via line 53 and recovered. A liquid hydrocarbonaceous stream is removed from fractionation zone 20 via line 21 and introduced into fractionation zone 22. A stream containing benzene and toluene is removed from fractionation zone 22 via line 24 and a portion is transported via lines 51 and 14 and introduced into reforming/transalkylation zone 15. Another portion of the stream containing benzene and toluene is removed from fractionation zone 22 via lines 24 and 60, and recovered. A liquid stream containing $C_8^+$ aromatic compounds is removed from fractionation zone 22 via line 23 and introduced into fractionation zone 25. A stream containing xylenes is removed from fractionation zone 25 via line 26 and recovered. A sidecut stream containing $C_9$ and $C_{10}$ aromatic compounds is removed from fractionation zone 25 via line 50 and introduced via lines 50, 51 and 14 into reforming/transalkylation zone 15. In an alternative embodiment that is not illustrated specifically, the sidecut stream containing $C_9$ and $C_{10}$ aromatic compounds in line 50 bypasses the reforming part of zone 15 and is sent directly to the transalkylation part of zone 15.

A hydrocarbon stream containing $C_{10}^+$ aromatic compounds is removed from fractionation zone 25 via line 27 and introduced into fractionation zone 12 to produce an ultra low sulfur diesel stream transported via line 13 and removed from fractionation zone 12. Another hydrocarbon stream containing $C_8^+$ aromatic compounds is removed from fractionation zone 12 and passed via line 54 to a separation vessel 57. A hydrocarbon stream containing $C_8^+$ aromatic compounds is removed from separation vessel 57 via line 59 and passed to line 50. A vaporous stream containing normally gaseous hydrocarbons is removed from separation vessel 57 via line 58 and recovered.

A liquid hydrocarbon stream containing hydrocarbons boiling above the naphtha range is removed from fractionation zone 6 via line 33 and a portion is transported via lines 45 and 3 and introduced into hydrotreating/hydrocracking zone 4 as the hereinabove described liquid hydrocarbon recycle stream and another portion is transported via lines 34 and 35 and introduced into aromatics hydrogenation zone 36. A resulting effluent from aromatics hydrogenation zone 36 is transported via line 37, partially condensed and introduced into vapor liquid separator 38. A liquid hydrocarbon stream containing hydrocarbons boiling in the range greater than naphtha and having a low concentration of sulfur is removed from vapor liquid separator 38 via line 39 and introduced into fractionation zone 12. A hydrogen-rich gaseous stream is removed from vapor liquid separator 38 via line 40 and is joined by a hydrogen-rich gaseous stream which is provided via line 49 as previously described and the resulting admixture is transported via line 42 and introduced into recycle compressor 43. A resulting compressed hydrogen-rich gaseous stream is removed from recycle compressor 43 via line 55 and a portion is carried via lines 44, 2 and 3 and introduced into hydrotreating/hydrocracking zone 4 as hydrogen-rich recycle gas as hereinabove described and another portion is carried via line 41 and is joined by a hydrogen-rich gaseous stream provided via line 31 as described hereinabove and the resulting admixture is transported via line 35 and introduced into aromatics hydrogenation zone 36. A hydrogen-rich gaseous stream is provided via lines 31 and 32 and optionally introduced into fractionation zone 8. Another hydrogen-rich gaseous stream is provided via lines 31 and 56 and optionally introduced into fractionation zone 6.

The foregoing description and drawing clearly illustrate the advantages encompassed by the process of the present invention and the benefits to be afforded with the use thereof.

What is claimed is:

1. A process for the production of low sulfur diesel and aromatic compounds which process comprises:
   (a) contacting a hydrocarbonaceous stream comprising $C_9^+$ hydrocarbons with a hydrocracking catalyst in a hydrocracking zone under hydrocracking conditions to produce a hydrocracking zone effluent comprising xylenes;
   (b) passing the hydrocracking zone effluent into a fractionation zone to produce a first stream comprising hydrocarbons boiling in the range from about 38° C. (100° F.) to about 220° C. (428° F.) and a second stream comprising hydrocarbons boiling above about 220° C. (428° F.);
   (c) contacting at least a portion of the first stream with a reforming catalyst in a reforming zone under reforming conditions to produce a reforming zone effluent comprising hydrogen and aromatic compounds;
   (d) optionally contacting at least a portion of the reforming zone effluent with a transalkylation catalyst in a transalkylation zone under transalkylation conditions to produce a liquid hydrocarbonaceous transalkylation effluent and a gaseous stream comprising hydrogen;
   (e) passing at least a portion of the hydrogen produced in step (c) to the hydrocracking zone; and
   (f) recovering xylenes.

2. The process of claim 1 wherein the hydrocarbonaceous stream comprising $C_9^+$ hydrocarbons comprises light cycle oil.

3. The process of claim 1 wherein the fractionation zone is a hot, high pressure stripper operating at a temperature from about 149° C. (300° F.) to about 288° C. (550° F.) and a pressure from about 3.5 MPa (500 psig) to about 17.3 MPa (2500 psig).

4. The process of claim 1 wherein the hydrocracking conditions comprise a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 hr$^{-1}$ and a hydrogen circulation rate from about 84 nm$^3$/m$^3$ (500 standard cubic feet per barrel) to about 4200 nm$^3$/m$^3$ (25,000 standard cubic feet per barrel).

5. The process of claim 1 wherein the reforming conditions comprise a pressure from about 100 kPa (14.7 psig) to about 7 MPa (1000 psig), a temperature from about 177° C. (350° F.) to about 565° C. (1049° F.), and a liquid hourly space velocity from about 0.2 to about 20 hr$^{-1}$.

6. The process of claim 1 wherein the transalkylation zone is present and transalkylation conditions comprise a temperature from about 200° C. (392° F.) to about 540° C. (1004° F.), a pressures from about 100 kPa (14.7 psig) to about 6 MPa (870 psig), and a liquid hourly space velocity from about 0.1 to about 20 hr$^{-1}$.

7. The process of claim 1 wherein the hydrocracking zone contains hydrocracking catalyst and hydrotreating catalyst.

8. The process of claim 1 wherein the reforming zone contains reforming catalyst and guard bed adsorbent.

9. The process of claim 1 further comprising the steps of recovering diesel and recovering gasoline comprising aromatic compounds.

10. A process for the production of low sulfur diesel and aromatic compounds which process comprises:
    (a) reacting a hydrocarbonaceous stream comprising $C_9^+$ hydrocarbons in a hydrocracking zone containing a hydrocracking catalyst to produce a hydrocracking zone effluent comprising xylenes;
    (b) passing the hydrocracking zone effluent into a fractionation zone to produce an first stream comprising hydrocarbons boiling in the range from about 38° C. (100° F.) to about 220° C. (428° F.) and a second stream comprising hydrocarbons boiling above about 220° C. (428° F.);
    (c) reacting at least a portion of the first stream produced in step (b) in a reforming-transalkylation zone to produce a liquid hydrocarbonaceous transalkylation effluent and a gaseous stream comprising hydrogen;
    (d) passing at least a portion of the gaseous stream comprising hydrogen produced in step (c) to the hydrocracking zone;
    (e) passing at least a portion of the second stream produced in step (b) to the hydrocracking zone; and
    (f) recovering xylenes.

11. The process of claim 10 wherein the hydrocarbonaceous stream comprising $C_9^+$ hydrocarbons comprises light cycle oil.

12. The process of claim 10 wherein the fractionation zone is a main fractionation column.

13. The process of claim 10 wherein the hydrocracking zone is operating at conditions including a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 hr$^{-1}$ and a hydrogen circulation rate from about 84 nm$^3$/m$^3$ (500 standard cubic feet per barrel) to about 4200 nm$^3$/m$^3$ (25,000 standard cubic feet per barrel).

14. The process of claim 10 wherein the reforming-transalkylation zone is operating at conditions including a temperature from about 177° C. (350° F.) to about 550° C. (1022° F.) and a liquid hourly space velocity from about 0.2 to about 10 hr$^{-1}$.

15. The process of claim 1 wherein the reforming-transalkylation zone contains reforming catalyst, transalkylation catalyst, and optional guard bed adsorbent.

16. A process for the production of low sulfur diesel and aromatic compounds which process comprises:
    (a) reacting a hydrocarbonaceous stream comprising $C_9^+$ hydrocarbons in a hydrocracking zone containing a hydrocracking catalyst to produce a hydrocracking zone effluent comprising xylenes;
    (b) passing the hydrocracking zone effluent into a fractionation zone to produce an overhead stream comprising hydrocarbons boiling in the range from about 38° C. (100° F.) to about 220° C. (428° F.) and a liquid stream comprising hydrocarbons boiling above about 220° C. (428° F.);
    (c) condensing at least a portion of the overhead stream comprising hydrocarbons boiling in the range from about 38° C. (100° F.) to about 220° C. (428° F.) to produce a liquid hydrocarbon stream;
    (d) separating and reacting at least a portion of the liquid hydrocarbon stream produced in step (c) in a reforming-transalkylation zone to produce a liquid hydrocarbonaceous transalkylation effluent and a gaseous stream comprising hydrogen;
    (e) passing at least a portion of the gaseous stream comprising hydrogen produced in step (d) to the hydrocracking zone;
    (f) reacting at least a portion of the liquid hydrocarbon stream comprising hydrocarbons boiling above 220° C. (428° F.) produced in step (b) in an aromatic hydrogenation reaction zone; and
    (g) recovering xylenes.

17. The process of claim 16 wherein the hydrocarbonaceous stream comprising $C_9^+$ hydrocarbons comprises light cycle oil.

18. The process of claim 16 wherein the hydrocracking zone is operating at conditions including a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 hr$^{-1}$ and a hydrogen circulation rate from about 84 nm$^3$/m$^3$ (500 standard cubic feet per barrel) to about 4200 nm$^3$/m$^3$ (25,000 standard cubic feet per barrel).

19. The process of claim 16 wherein the integrated reforming-transalkylation zone is operating at conditions including a temperature from about 177° C. (350° F.) to about 550° C. (1022° F.) and a liquid hourly space velocity from about 0.2 to about 10 hr$^{-1}$.

20. The process of claim 16 wherein the hydrocracking zone contains hydrocracking catalyst and hydrotreating catalyst.

21. The process of claim 16 further comprising the step of recovering low sulfur diesel.

22. The process of claim 16 wherein the reforming-transalkylation zone contains reforming catalyst, transalkylation catalyst, and optional guard bed adsorbent.

23. The process of claim 16 wherein at least a portion of the liquid stream comprising hydrocarbons boiling above about 220° C. (428° F.) produced in step (b) is recycled to the hydrocracking zone.

24. The process of claim 16 wherein step (g) further comprises recovering gasoline.

25. The process of claim 16 wherein the reforming-transalkylation zone comprises a reforming zone and a transalkylation zone, and step (d) further comprises bypassing at least a portion of the liquid hydrocarbon stream around the reforming zone and passing said portion of the liquid hydrocarbon stream to the transalkylation zone.

\* \* \* \* \*

UNITED STATES PATENT AND TRADEMARK OFFICE
CERTIFICATE OF CORRECTION

| | | |
|---|---|---|
| PATENT NO. | : 7,271,303 B1 | Page 1 of 1 |
| APPLICATION NO. | : 10/946928 | |
| DATED | : September 18, 2007 | |
| INVENTOR(S) | : Paul A. Sechrist et al. | |

It is certified that error appears in the above-identified patent and that said Letters Patent is hereby corrected as shown below:

Column 14,
Line 35, Claim 15, replace "The process of claim 1" with --The process of claim 10--.

Signed and Sealed this

Twenty-second Day of July, 2008

JON W. DUDAS
*Director of the United States Patent and Trademark Office*